(12) United States Patent
Ha et al.

(10) Patent No.: US 7,888,511 B2
(45) Date of Patent: Feb. 15, 2011

(54) METHOD OF PREPARING ESOMEPRAZOLE AND SALTS THEREOF

(75) Inventors: Tae Hee Ha, Suwon-si (KR); Won Jeong Kim, Suwon-si (KR); Hee Sook Oh, Seoul (KR); Chang Hee Park, Yongin-si (KR); Jae Chul Lee, Suwon-si (KR); Han Kyong Kim, Yongin-si (KR); Kwee-Hyun Suh, Suwon-si (KR)

(73) Assignee: Hanmi Holdings Co., Ltd., Seoul (KR)

( * ) Notice: Subject to any disclaimer, the term of this patent is extended or adjusted under 35 U.S.C. 154(b) by 595 days.

(21) Appl. No.: 11/996,657

(22) PCT Filed: Jul. 11, 2006

(86) PCT No.: PCT/KR2006/002719

§ 371 (c)(1),
(2), (4) Date: Jan. 24, 2008

(87) PCT Pub. No.: WO2007/013743

PCT Pub. Date: Feb. 1, 2007

(65) Prior Publication Data

US 2008/0194828 A1    Aug. 14, 2008

(30) Foreign Application Priority Data

Jul. 28, 2005    (KR) ...................... 10-2005-0068761

(51) Int. Cl.
*C07D 401/12* (2006.01)
(52) U.S. Cl. .................................................. 546/273.7
(58) Field of Classification Search ............... 546/273.7
See application file for complete search history.

(56) References Cited

FOREIGN PATENT DOCUMENTS

| WO | WO 94/27988 A1 | 12/1994 |
|----|----------------|---------|
| WO | WO 2004/002982 A2 | 1/2004 |
| WO | 2006094904 A1 | 2/2006 |

OTHER PUBLICATIONS

Deng, J. et al., "Resolution of omeprazole by inclusion complexation with a chiral host BINOL," Tetrahedron: Asymmetry, 2000, vol. 11, pp. 1729-1732.

*Primary Examiner*—Patricia L Morris
(74) *Attorney, Agent, or Firm*—Sughrue Mion, PLLC

(57) ABSTRACT

Optically pure esomeprazole and its salt can be simply prepared by dissolving (S)-(−)-binol, a weak base and the racemic form of omeprazole in a mixture of a water-compatible organic solvent and water at a high temperature, cooling the mixed solution to crystallize the inclusion complex of esomeprazole and (S)-(−)-binol, and removing the (S)-(−)-binol moiety from the crystallized inclusion complex.

14 Claims, 2 Drawing Sheets

Example 1            Comparative Example 3

METHOD OF PREPARING ESOMEPRAZOLE AND SALTS THEREOF

FIELD OF THE INVENTION

The present invention relates to a method of preparing optically pure esomeprazole, and its salt, from omeprazole by applying an improved optical resolution process.

BACKGROUND OF THE INVENTION

Esomeprazole of formula (II), the levorotatory isomer of racemic omeprazole, is an ulcer treating agent which is very effective in treating such disorders as gastric ulcer, duodenal ulcer and reflux esophagitis, which is less influenced by liver metabolism, exerting less adverse effect, as compared to the omeprazole racemate. It is now commercially available in the form of Nexium®:

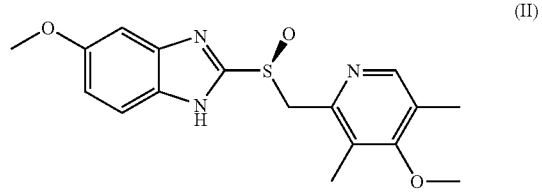

Various methods of preparing esomeprazole are described in the literatures, e.g., U.S. Pat. Nos. 5,693,818 and 6,369,085, International Publication Patent Nos. WO 1996/002535, WO 1997/002261 and WO 2004/002982, Chinese Patent No. 1,087,739, [J. Deng et al., Tetrahedron: *Asymmetry*, 11, 1729-1732, 2000] and [H. Cotton et al., Tetrahedron: *Asymmetry*, 11, 3819-3825, 2000]. Among these methods, preferred in terms of commercial applicability are methods which involve resolving racemic omeprazole using an optical resolution agent or asymmetrically oxidizing a precursor of esomeprazole using a chiral reagent.

For example, Chinese Patent No. 1,087,739 discloses a method of preparing esomeprazole of formula (II) by way of reacting the racemic form of omeprazole with (S)-(−)-binol (a levorotatory isomer of β-binaphthol) as an optical resolution agent to form the inclusion complex of esomeprazole and (S)-(−)-binol of formula (I), and removing the (S)-(−)-binol moiety therefrom:

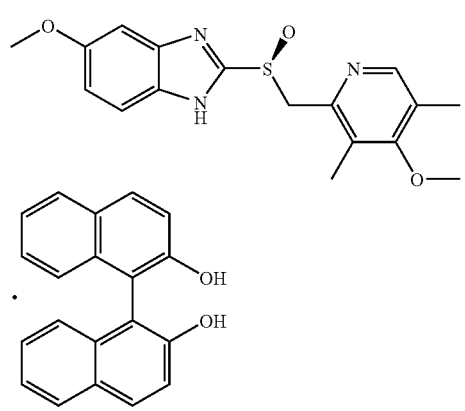

However, this method has several problems in that;

1) for the purpose of obtaining esomeprazole of a high optical purity, relatively expensive (S)-(−)-binol must be used in an excess amount of 1.5 mole equivalents based on omeprazole, 2) benzene (Class I; ICH Q3C Impurities: Guideline for Residual Solvents (CPMP/ICH/283/95)) which has potential to instigate toxicity is used as a solvent in the method, 3) the inclusion complex of formula (I), and also the solution containing same are colored pitch-black, which requires a decolorization step in the recycling of unreacted (S)-(−)-binol isolated from the reaction mixture containing the inclusion complex, 4) the removal of (S)-(−)-binol from the inclusion complex of formula (I) is performed by chromatography, which is not suitable for mass production, and 5) the optical purity of the inclusion complex of formula (I) is unsatisfactorily low, i.e., about 90% ee (enantiomeric excess), which necessitates further purification of the final esomeprazole product, causing a lowering of the yield ([J. Deng et al., Tetrahedron: *Asymmetry*, 11, 1729-1732, 2000]).

SUMMARY OF THE INVENTION

Accordingly, it is a primary object of the present invention to provide an improved optical resolution process for preparing optically pure esomeprazole and its salt.

In accordance with one aspect of the present invention, there is provided a method of preparing esomeprazole of formula (II) or its salt having an optical purity of at least 98% ee, which comprises:

(A) dissolving (S)-(−)-binol, a weak base and the racemic form of omeprazole in a mixture of a water-compatible organic solvent and water at a temperature ranging from 30 to 70° C., and cooling the resulting solution to a temperature of −5° C. to room temperature to allow the crystallization of the inclusion complex of esomeprazole and (S)-(−)-binol of formula (I); and (B) removing the (S)-(−)-binol moiety from the inclusion complex of formula (I) obtained in step (A) by filtration or extraction:

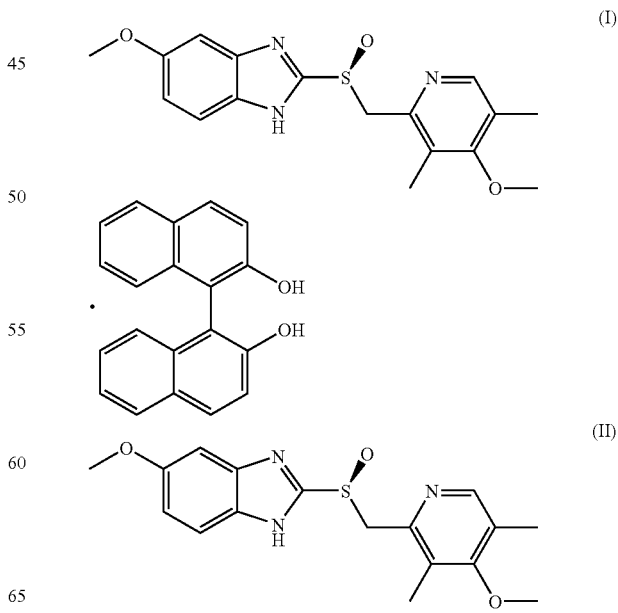

BRIEF DESCRIPTION OF THE DRAWINGS

The above and other objects and features of the present invention will become apparent from the following description of the invention taken in conjunction with the following accompanying drawings, which respectively show.

DETAILED DESCRIPTION OF THE INVENTION

Figure 1:
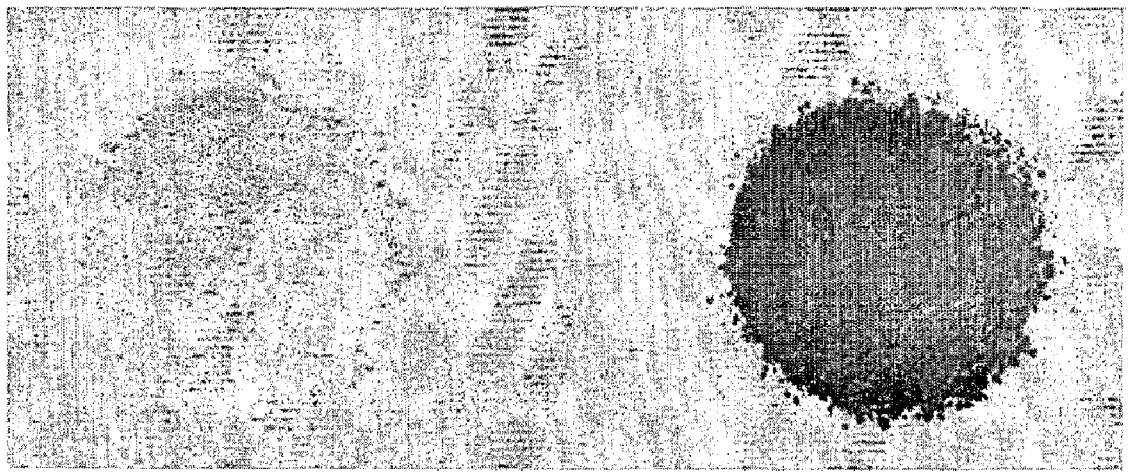
FIG. 1: photographs of the esomeprazole/(S)-(−)-binol inclusion complexes obtained in Example 1 and Comparative Example 3, respectively.

Step (A) in accordance with the present invention comprises dissolving (S)-(−)-binol as an optical resolution agent, a weak base and the racemic form of omeprazole in a mixture of a water-compatible organic solvent and water at a temperature ranging from 30 to 70° C., and then allowing the mixed solution to cool to a temperature of −5° C. to room temperature, preferably of 0 to 15° C., to crystallize the inclusion complex of esomeprazole and (S)-(−)-binol of formula (I).

The (S)-(−)-binol optical resolution agent may be used in an amount ranging from 0.5 to 0.7 mole equivalent based on omeprazole, which is much less than that used in conventional optical resolution processes.

The weak base used in the present invention prevents the inclusion complex of formula (I) from turning black and representative examples thereof include ammonium hydroxide, methylamine, ethylamine, dimethylamine, diethylamine, trimethylamine, triethylamine and a mixture thereof. The weak base may be used in an amount ranging from 0.05 to 1 mole equivalent, preferably from 0.1 to 0.5 mole equivalent, based on omeprazole.

The water-compatible organic solvent-water mixture used in the present invention may comprise the organic solvent and water in a volume ratio of 98~40:2~60. If necessary, additional water may be added to the mixed solvent just before cooling so long as the final mixture satisfies the above-mentioned volume ratio. The water-compatible organic solvent, which is non-toxic, may be methanol, ethanol, 1-propanol, 2-propanol, 1-butanol, 2-butanol, acetone, acetonitrile, 1,4-dioxane or a mixture thereof (Class II or III; ICH Q3C Impurities: Guideline for Residual Solvents (CPMP/ICH/283/95)), which may be used in an amount of 3 to 15 ml based on 1 g of omeprazole.

The esomeprazole/(S)-(−)-binol inclusion complex of formula (I) crystallized by cooling may be obtained in a crystalline powder form through the conventional filtering or drying method. The white or white-yellow crystalline inclusion complex thus obtained has a satisfactory optical purity of at least 95% ee, which does not require further purification, but, if necessary, it may be further recrystallized from a mixture of a water-compatible organic solvent and water to further improve its purity.

Step (B) in accordance with the present invention comprises removing the (S)-(−)-binol moiety from the inclusion complex of formula (I) obtained in step (A) by filtration or extraction to obtain esomeprazole of formula (II) or its salt.

Specifically, in step (B), esomeprazole of formula (II) or its salt may be obtained by suspending the inclusion complex of formula (I) in water or alcohol and adding a base thereto, followed by filtration or extraction with an organic solvent, to separate the (S)-(−)-binol moiety from the inclusion complex. This step (B) may be performed at room temperature.

When the inclusion complex of formula (I) is suspended in water, as the base, sodium hydroxide or potassium hydroxide may be used in an amount ranging from 1 to 1.5 mole equivalents, preferably from 1 to 1.2 mole equivalents, based on the inclusion complex. In this case, (S)-(−)-binol is isolated in the subsequent filtration or extraction step and esomeprazole of formula (II) or its salt may be recovered from the alkaline filtrate by the conventional methods. For example, esomeprazole may be recovered by acidifying the filtrate using acetic acid, followed by filtration or extraction with an organic solvent; sodium or potassium salt of esomeprazole, by concentrating the filtrate and adding an organic solvent to the concentrate to induce the crystallization of the desired product, or by acidifying the filtrate using acetic acid, extracting it with an organic solvent and adding sodium or potassium hydroxide to the resulting organic layer to induce the crystallization of the desired product; and magnesium salt of esomeprazole, by adding an aqueous magnesium chloride solution to the filtrate containing sodium or potassium salt of esomeprazole, or to an aqueous solution of sodium or potassium salt of esomeprazole previously obtained, to induce the crystallization of the desired product.

On the other hand, when the inclusion complex of formula (I) is suspended in alcohol such as methanol, ethanol and isopropanol, strontium hydroxide is suitable for use as the base and it may be used in an amount ranging from 0.5 to 0.75 mole equivalent, preferably from 0.5 to 0.6 mole equivalent, based on the inclusion complex. In this case, strontium salt of esomeprazole is directly isolated in the subsequent filtration or extraction step and (S)-(−)-binol may be recovered from the alkaline filtrate for further recycling by the conventional methods. For example, (S)-(−)-binol may be recovered by adding water to the filtrate, followed by filtration.

The organic solvent suitable for use in the extraction step may be methyl acetate, ethyl acetate, isopropyl acetate, ethyl ether, dichloromethane, chloroform or a mixture thereof.

The (S)-(−)-binol thus isolated may be recovered in a yield of 85% or higher. As it is not colored black, it may be reused in the preparation of the inclusion complex of formula (I) via a simple purification procedure including a recrystallization step.

Esomeprazole or its salt obtained in accordance with the inventive method has a high optical purity of at least 98% ee, which meets the minimum pharmaceutical purity required by US Pharmacopoeia.

As described above, the method of the present invention can be advantageously used for simple and economical preparation of optically pure esomeprazole and its salt, without the problem of coloration which prevents the recycling of (S)-(−)-binol optical resolution agent.

The following Examples are given for the purpose of illustration only, and are not intended to limit the scope of the invention.

The optical purities of the respective esomeprazole/(S)-(−)-binol inclusion complexes, and esomeprazole and its salt, obtained in the following Examples and Comparative Examples were determined by chiral HPLC (high performance liquid chromatography) under the conditions listed below:

column: Chiral-AGP (5 μm, 150 mm×4 mm)
detection wavelength: 280 nm
flow rate: 0.8 ml/min
eluent: 10% acetonitrile-phosphate buffer of pH 6.5

<Preparation of Inclusion Complex of Esomeprazole and (S)-(−)-binol (Formula (I))>

Example 1

25.0 g of (S)-(−)-binol (87.3 mmol) was dissolved in a mixture of 400 ml of ethanol and 100 ml of water at 60° C., and 5.0 ml of triethylamine (35.9 mmol) and 50.0 g of the racemic form of omeprazole (144.8 mmol) were dissolved thereto while maintaining the temperature at 50-55° C. Then, the resulting solution was slowly cooled to room temperature and stirred at that temperature for 12 hrs. The precipitated solids were filtered, washed sequentially with a mixture of 85 ml of ethanol and 15 ml of water and with 100 ml of n-hexane, and dried at 40° C. to obtain 38.9 g of the white-yellow title compound (yield: 85%).

M.p.: 158-160° C.
Specific linear luminosity: $[\alpha]_D^{20}$=−146.2° (c=1, THF).
Optical purity: 98.7% ee (chiral HPLC).
$^1$H-NMR (CDCl$_3$, ppm): δ 2.24 (s, 6H), 3.73 (s, 3H), 3.87 (s, 3H), 4.65 (d, 1H), 4.78 (d, 2H), 5.50 (br. s, 2H), 6.96 (br. s, 2H), 7.18 (d, 2H), 7.40-7.28 (m, 8H), 7.70 (br. s, 1H), 7.90 (d, 2H), 7.98 (d, 2H), 8.16 (s, 1H), 11.60 (bs, 1H).
IR (KBr, cm$^{-1}$): 3057, 1619, 1595, 1576, 1471, 1462, 1401, 1380, 1271, 1205, 1146, 1073, 1028, 815, 570, 506, 422.

Example 2

99.6 g of (S)-(−)-binol (0.35 mol) was dissolved in a mixture of 1200 ml of isopropanol and 200 ml of water at 60° C., and 10 ml of 28% ammonia (0.15 mol) and 200.0 g of the racemic form of omeprazole (0.58 mol) were added thereto while maintaining the temperature at 50-55° C. 600 ml of water was slowly added to the resulting solution and after the complete dissolution of the contents was achieved, 0.2 g of the inclusion complex of esomeprazole and (S)-(−)-binol was added as a seed thereto. The resulting solution was slowly cooled to room temperature and stirred for 6 hrs, and further cooled to 5-10° C. and stirred for 4 hrs. The precipitated solids were filtered, washed sequentially with a mixture of 160 ml of isopropanol and 40 ml of water and with 200 ml of n-hexane, and dried at 40° C. to obtain 163.1 g of the white-yellow title compound (yield: 89%). The proton nuclear magnetic resonance ($^1$H-NMR) and infrared ray (IR) spectra of the product were identical to those obtained in Example 1.

M.p.: 157-159° C.
Specific linear luminosity: $[\alpha]_D^{20}$=−145.9° (c=1, THF).
Optical purity: 96.8% ee (chiral HPLC).

Examples 3 to 14

The procedure of Example 1 or 2 was repeated employing 50.0 g of the racemic form of omeprazole (144.8 mmol), 500 ml of a reaction solvent and the other specifics shown in Table 1, to obtain various compounds, whose yields and optical purities are listed in Table 1.

TABLE 1

| Ex. No. | Reaction solvent (v/v) | (S)-(−)-binol (mole eq.) | Base (mole eq.) | Amount of title compound, g (yield, %) | Optical purity (% ee) |
|---|---|---|---|---|---|
| 3 | ethanol/water(95/5) | 0.60 | NH$_4$OH(0.25) | 36.6 (80) | 98.8 |
| 4 | ethanol/water(70/30) | 0.60 | NH$_4$OH(0.25) | 40.3 (88) | 98.0 |
| 5 | ethanol/water(70/30) | 0.50 | NH$_4$OH(0.25) | 38.9 (85) | 97.9 |
| 6 | ethanol/water(70/30) | 0.60 | NH$_4$OH(0.10) | 41.2 (90) | 96.2 |
| 7 | ethanol/water(70/30) | 0.60 | NH$_4$OH(0.50) | 38.4 (84) | 97.0 |
| 8 | ethanol/water(70/30) | 0.60 | EtNH$_2$(0.25) | 40.7 (89) | 96.7 |
| 9 | ethanol/water(60/40) | 0.60 | NH$_4$OH(0.25) | 42.1 (92) | 95.6 |
| 10 | methanol/water(70/30) | 0.60 | NH$_4$OH(0.25) | 38.0 (83) | 98.5 |
| 11 | 1-butanol/water(70/30) | 0.60 | NH$_4$OH(0.25) | 38.9 (85) | 97.2 |
| 12 | acetone/water(60/40) | 0.60 | NH$_4$OH(0.25) | 38.9 (86) | 96.3 |
| 13 | acetonitrile/water(60/40) | 0.60 | NH$_4$OH(0.25) | 38.0 (81) | 95.7 |
| 14 | 1,4-dioxane/water(50/50) | 0.60 | NH$_4$OH(0.25) | 18.3 (40) | 97.7 |

Example 15

Purification of Inclusion Complex of Esomeprazole and (S)-(−)-binol (Formula (I))

50.0 g of the inclusion complex of formula (I) having an optical purity of 95-98% ee was added to a mixture of 255 ml of isopropanol and 45 ml of water in which 1.0 ml of 28% ammonia was dissolved, and stirred at 50-55° C. for 4 hrs, which was slowly cooled to 5-10° C. and stirred for 12 hrs. The precipitated solids were filtered, washed sequentially with a mixture of 85 ml of isopropanol and 15 ml of water and with 100 ml of n-hexane, and dried at 40° C. for 3 hrs to obtain 44 g of the white-yellow and optically pure title compound (yield: 88%). The proton nuclear magnetic resonance ($^1$H-NMR) and infrared ray (IR) spectra of the product were identical to those obtained in Example 1.

M.p.: 158-161° C.
Specific linear luminosity: $[\alpha]_D^{20}$=−147.3° (c=1, THF).
Optical purity: 99.4% ee (chiral HPLC).

Preparation of Esomeprazole (Formula (II)) or its Salt

Example 16

Preparation of Esomeprazole 65.0 g of the inclusion complex (optical purity: 99.4% ee) of esomeprazole and (S)-(−)-binol obtained in Example 15, and 300 ml of isopropyl acetate were added sequentially to 300 ml of an aqueous solution containing 4.95 g of sodium hydroxide, which was stirred at room temperature for 30 min. The organic layer was separated and the aqueous layer was further extracted with 150 ml of isopropyl acetate. The organic layers were combined and concentrated to recover 25 g of (S)-(−)-binol therefrom (recovery ratio: 85%). To the aqueous layer, on the other hand, 300 ml of dichloromethane was added, the pH of the resulting mixture was adjusted to 8.0 with 1N acetic acid, and the organic layer was separated. The organic layer was dried over anhydrous magnesium sulfate and concentrated under a reduced pressure to obtain 33.7 g of the title compound in the form of a foaming material (yield: 95%).

Specific linear luminosity: $[\alpha]_D^{20}=-146.9°$ (c=1, THF).

Optical purity: 99.4% ee (chiral HPLC).

$^1$H-NMR (CDCl$_3$, ppm): δ 2.14 (s, 3H), 2.24 (s, 3H), 3.72 (s, 3H), 3.86 (s, 3H), 4.76 (dd, 2H), 6.96 (dd, 1H), 7.04 (br. s, 1H), 7.29 (s, 1H), 7.56 (br. s, 1H), 8.23 (s, 1H).

IR (KBr, cm$^{-1}$): 3529, 3349, 1628, 1590, 1571, 1465, 1414, 1398, 1270, 1211, 1156.4, 1079, 1048, 1029, 837, 625, 518.

Example 17

Preparation of Esomeprazole 65.0 g of the inclusion complex (optical purity: 99.4% ee) of esomeprazole and (S)-(−)-binol obtained in Example 15, and 300 ml of isopropyl acetate were added sequentially to 300 ml of an aqueous solution containing 4.95 g of sodium hydroxide, which was stirred at room temperature for 30 min. The organic layer was separated and the aqueous layer was further extracted with 150 ml of isopropyl acetate. Then, 30 ml of isopropyl alcohol was added to the aqueous layer, the pH of the resulting mixture was adjusted to 8.0 with 1N acetic acid and stirred at 5-10° C. for 20 hrs. The precipitated solids were filtered, washed sequentially with 100 ml of water and 100 ml of n-hexane, and dried at room temperature under a reduced pressure, to obtain 30.9 g of the title compound as a white-yellow solid (yield: 87%). The proton nuclear magnetic resonance ($^1$H-NMR) and infrared ray (IR) spectra of the product were identical to those obtained in Example 16.

M.p.: 70° C.

Specific linear luminosity: $[\alpha]_D^{20}=-150.7°$ (c=0.5, CHCl$_3$).

Optical purity: 99.5% ee (chiral HPLC).

Example 18

Preparation of Sodium Salts of Esomeprazole 65.0 g of the inclusion complex of esomeprazole and (S)-(−)-binol having an optical purity of 95.2% ee, and 300 ml of isopropyl acetate were added sequentially to 300 ml of an aqueous solution containing 4.95 g of sodium hydroxide, which was stirred at room temperature for 30 min. The organic layer was separated and the aqueous layer was further extracted with 150 ml of isopropyl acetate. The aqueous layer was distilled under a reduced pressure to remove water. 20 ml of methyl isobutyl ketone and 80 ml of acetonitrile were added to the resulting residue, which was stirred. The precipitated solids were filtered and dried at 40° C. to obtain 34.1 g of the title compound as a white crystalline powder (yield: 90%).

M.p.: 238-240° C.

Water content: 4.87%

Specific linear luminosity: $[\alpha]_D^{20}=+29.9°$ (c=0.5, H$_2$O).

Optical purity: 99.6% ee (chiral HPLC).

$^1$H-NMR (DMSO-d$_6$, ppm): δ 2.21 (s, 6H), 3.69 (s, 3H), 3.73 (s, 3H), 4.38 (d, 1H, J=12.9 Hz), 4.68 (d, 1H, J=12.9 Hz), 6.54 (dd, 2H, J=8.5 Hz and J=2.3 Hz), 6.98 (d, 1H, J=2.3 Hz), 7.32 (d, 1H, J=8.5 Hz), 8.23 (s, 1H).

IR (KBr, cm$^{-1}$): 2936, 2828, 2615, 2655, 2056, 1651, 1644, 1614, 1574, 1568, 1557, 1479, 1472, 1455, 1372, 1361, 1295, 1269, 1199, 1153, 1077, 1019, 1000, 952, 867, 414.

Example 19

Preparation of Potassium Salts of Esomeprazole 65.0 g of the inclusion complex of esomeprazole and (S)-(−)-binol having an optical purity of 96.5% ee, and 300 ml of isopropyl acetate were added sequentially to 300 ml of an aqueous solution containing 6.35 g of potassium hydroxide, which was stirred at room temperature for 30 min. The organic layer was separated and the aqueous layer was further extracted with 150 ml of isopropyl acetate. The aqueous layer was distilled under a reduced pressure to remove water. 200 ml of methanol and 20 ml of toluene were added to the resulting residue, which was stirred. The precipitated solids were filtered and dried at 40° C. to obtain 33.54 g of the title compound as a white crystalline monohydrate powder (yield: 85%).

M.p.: 118-120° C.

Water content: 3.54%

Specific linear luminosity: $[\alpha]_D^{20}=+27.8°$ (c=1, H$_2$O).

Optical purity: 99.8% ee (chiral HPLC).

$^1$H-NMR (CDCl$_3$, ppm): δ 2.21 (s, 6H), 3.69 (s, 3H), 3.74 (s, 3H), 4.43 (d, 1H, J=12.9 Hz), 4.75 (d, 1H, J=12.9 Hz), 6.59 (dd, 2H, J=8.6 Hz and J=1.8 Hz), 7.00 (d, 1H, J=1.8 Hz), 7.34 (d, 1H, J=8.6 Hz), 8.22 (s, 1H).

IR (KBr, cm$^{-1}$): 2830, 2361, 2344, 1614, 1592, 1570, 1478, 1445, 1397, 1362, 1296, 1270, 1200, 1154, 1075, 1027, 953, 842, 804, 632, 522, 439.

Example 20

Preparation of Magnesium Salts of Esomeprazole 65.0 g of the inclusion complex of esomeprazole and (S)-(−)-binol having an optical purity of 98.7% ee, and 300 ml of isopropyl acetate were added sequentially to 300 ml of an aqueous solution containing 4.95 g of sodium hydroxide, which was stirred at room temperature for 30 min. The organic layer was separated and the aqueous layer was further extracted with 150 ml of isopropyl acetate. 150 ml of an aqueous solution containing 5.0 g of magnesium chloride was added to the aqueous layer and the resulting suspension was stirred for 1 hr. The precipitated solids were filtered, washed with water and dissolved in 100 ml of methanol. 400 ml of acetone was added to the resulting solution and stirred at room temperature for 2 hrs. The precipitated solids were filtered and dried at 40° C. to obtain 31.6 g of the title compound as a white crystalline dihydrate powder (yield: 82%).

M.p.: 174-177° C.

Water content: 5.12% (2H$_2$O: 4.81%).

Optical purity: 99.6% ee (chiral HPLC).

IR (KBr, cm$^{-1}$): 3070, 2994, 2939, 2830, 1615, 1590, 1570, 1477, 1436, 1409, 1303, 1272, 1200, 1156, 1078, 1029, 1003, 956, 835, 806, 770, 632, 580.

Example 21

Preparation of Strontium Salt of Esomeprazole 153.0 g of the inclusion complex of esomeprazole and (S)-(−)-binol having an optical purity of 98.3% ee was dissolved in 1000 ml of methanol, and strontium hydroxide (37.3 g as octahydrate) was added thereto, followed by stirring the resulting mixture at room temperature for 3 hours. The precipitate formed was filtered, washed with 300 ml of methanol and dried at 45° C. for 12 hours, to obtain 93.0 g of the title compound as an white crystalline powder (yield: 93%). Then, 3000 ml of water was added to the filtrate and the mixture was stirred for several hours at room temperature. The precipitated solids were recovered by filtration, followed by washing with water, to afford 63.0 g of (S)-(−)-binol (yield: 90%).

M.p.: 201-203° C.

Water content: 9.0% (4H$_2$O: 8.49%).

Optical purity: 99.9% ee (chiral HPLC).

$^1$H-NMR (DMSO-d$^6$): δ 8.26 (s, 1H), 7.38 (d, 1H), 7.02 (bs, 1H), 6.54 (dd, 1H), 4.58 (d, 2H, J=13.3), 4.46 (d, 2H, J=13.4), 3.68 (s, 3H), 3.66 (s, 3H), 2.22 (s, 3H), 2.10 (s, 3H).

IR (KBr, cm$^{-1}$): 3422, 2991, 2831, 2364, 1638, 1611, 1569, 1561, 1476, 1444.4, 1390, 1365, 1271, 1204, 1156, 1077, 1027, 1000, 855, 844, 798, 637, 487.

Comparative Examples 1 to 3

Preparation of Inclusion Complex of esomeprazole and (S)-(−)-binol (Formula (I)) in Accordance with the Method Disclosed in [J. Deng et al., Tetrahedron: *Asymmetry*, 11, 1729-1732, 2000] and [H. Cotton et al., Tetrahedron: *Asymmetry*, 11, 3819-3825, 2000]

(S)-(−)-binol and 10.0 g of the racemic form of omeprazole were dissolved in a mixture of 288 ml of benzene and 72 ml of n-hexane at 110° C. The (S)-(−)-binol was used in the amount of each of 0.6, 1.0 and 1.5 mole equivalents based on omeprazole, as shown in Table 2. Then, the resulting solution was slowly cooled to 0° C. and stirred for 12 hrs. The precipitated solids were filtered, and washed with a mixture of benzene and hexane to obtain the title compound.

The optical purities and/or colors of the products thus obtained were shown in Table 2 and FIG. 1, together with those of the product obtained in Example 1.

TABLE 2

| | Amount of (S)-(−)-binol (mole eq.) | Optical purity (% ee) | Color |
|---|---|---|---|
| Ex. 1 | 0.6 | 98.7 | White-yellow |
| Comp. Ex. 1 | 0.6 | 20.0 | Yellow |
| Comp. Ex. 2 | 1.0 | 82.6 | Black |
| Comp. Ex. 3 | 1.5 | 92.2 | Black |

As shown in Table 2 and FIG. 1, the inventive compound obtained in Example 1 was rarely colored and its optical purity is much higher as compared to those of the comparative compounds.

Test Example

Measurement of Absorbance at a Visible-Ray Region

Visible-ray absorbances of the respective esomeprazole/(S)-(−)-binol inclusion complexes obtained in Example 1, Comparative Example 2 and Comparative Example 3 were determined after each of them was dissolved in acetonitrile with 0.1% concentration, in accordance with the absorbance-measuring method disclosed in US Pharmacopoeia. The results were shown in Table 3 and FIG. 2.

TABLE 3

| | Absorbance | |
|---|---|---|
| | 402 nm | 540 nm |
| Comp. Ex. 2 | 0.392 | 0.313 |
| Comp. Ex. 3 | 0.510 | 0.368 |
| Ex. 1 | 0.010 | 0.001 |

Figure 2:
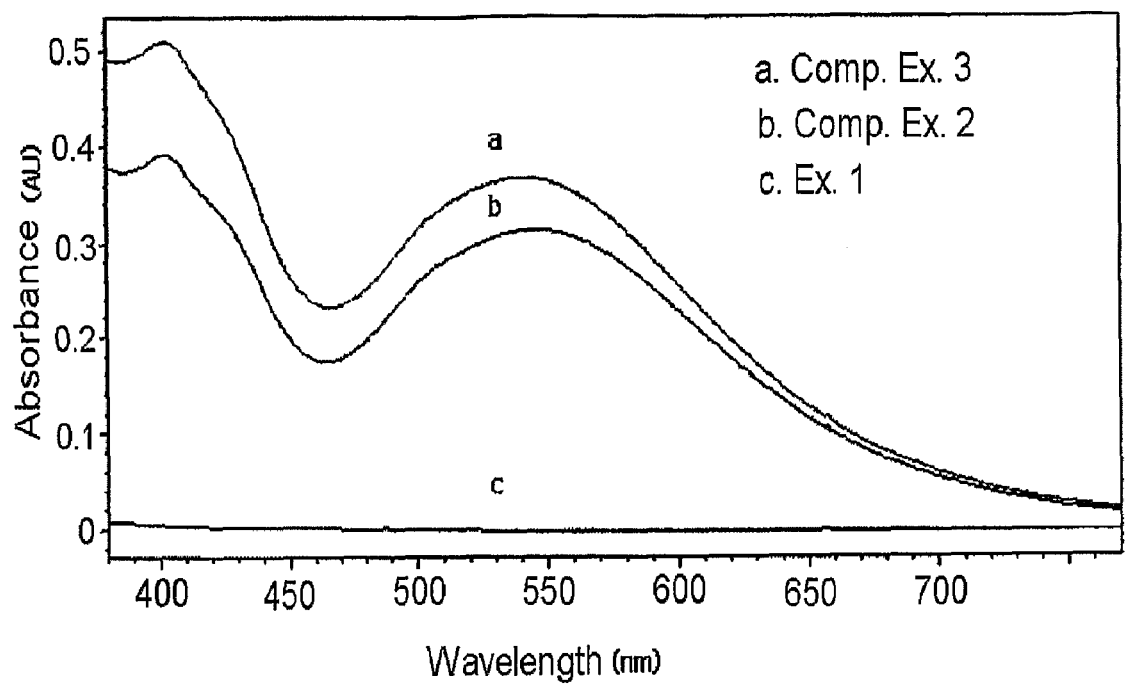
FIG. 2: visible-ray absorption spectra of the esomeprazole/(S)-(−)-binol inclusion complexes obtained in Example 1, Comparative Example 2 and Comparative Example 3, respectively.

The absorbances shown in Table 3 and FIG. 2 suggest that the inventive compound obtained in Example 1 was not colored, while the comparative compounds was seriously colored black.

As shown above, the method of the present invention is capable of providing optically pure esomeprazole and its salt, without the problem of coloration which prevents the recycling of (S)-(−)-binol optical resolution agent.

While the embodiments of the subject invention have been described and illustrated, it is obvious that various changes and modifications can be made therein without departing from the spirit of the present invention which should be limited only by the scope of the appended claims.

What is claimed is:

1. A method of preparing esomeprazole of formula (II) or its salt having an optical purity of at least 98% ee, which comprises:
   (A) dissolving (S)-(−)-binol, a weak base and the racemic form of omeprazole in a mixture of a water-compatible organic solvent and water at a temperature ranging from 30 to 70° C., and cooling the resulting solution to a temperature of −5° C. to room temperature to allow the crystallization of the inclusion complex of esomeprazole and (S)-(−)-binol of formula (I); and
   (B) removing the (S)-(−)-binol moiety from the inclusion complex of formula (I) obtained in step (A) by filtration or extraction:

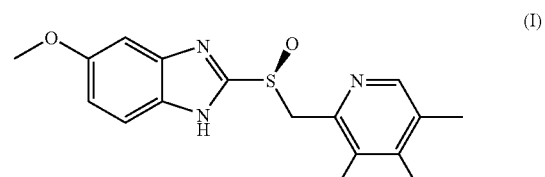

(I)

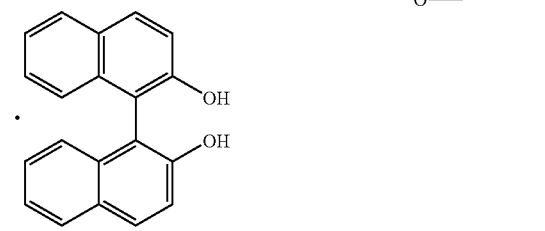

(II)

2. The method of claim 1, wherein the amount of (S)-(−)-binol used in step (A) is in the range of 0.5 to 0.7 mole equivalent based on omeprazole.

3. The method of claim 1, wherein the water-compatible organic solvent used in step (A) is selected from the group consisting of methanol, ethanol, 1-propanol, 2-propanol, 1-butanol, 2-butanol, acetone, acetonitrile, 1,4-dioxane and a mixture thereof.

4. The method of claim 1, wherein the volume ratio of the water-compatible organic solvent and water used in step (A) is in the range of 98~40:2~60.

5. The method of claim 1, wherein the volume of the water-compatible organic solvent employed in step (A) is in the range of 3 to 15 ml based on 1 g of omeprazole.

6. The method of claim 1, wherein the weak base used in step (A) is selected from the group consisting of ammonium hydroxide, methylamine, ethylamine, dimethylamine, diethylamine, trimethylamine, triethylamine and a mixture thereof.

7. The method of claim 1, wherein the amount of the weak base employed in step (A) is in the range of 0.05 to 1 mole equivalent based on omeprazole.

8. The method of claim 1, wherein the inclusion complex of esomeprazole and (S)-(−)-binol crystallized in step (A) has an optical purity of at least 95% ee.

9. The method of claim 1, wherein step (B) comprises suspending the inclusion complex of formula (I) obtained in step (A) in water or alcohol and adding a base thereto, followed by filtration or extraction with an organic solvent, to separate the (S)-(−)-binol moiety from the inclusion complex.

10. The method of claim 9, wherein when the inclusion complex of formula (I) is suspended in water, the base used in step (B) is sodium hydroxide or potassium hydroxide and its amount is in the range of 1 to 1.5 mole equivalents based on the inclusion complex.

11. The method of claim 9, wherein when the inclusion complex of formula (I) is suspended in alcohol, the base used in step (B) is strontium hydroxide and its amount is in the range of 0.5 to 0.75 mole equivalent based on the inclusion complex.

12. The method of claim 11, wherein alcohol is selected from the group consisting of methanol, ethanol and isopropanol.

13. The method of claim 9, wherein the organic solvent used in step (B) is selected from the group consisting of methyl acetate, ethyl acetate, isopropyl acetate, ethyl ether, dichloromethane, chloroform and a mixture thereof.

14. The method of claim 1, wherein the (S)-(−)-binol freed in step (B) is isolated for reuse in step (A).

* * * * *